United States Patent
Jang et al.

(10) Patent No.: US 11,590,061 B2
(45) Date of Patent: Feb. 28, 2023

(54) FLUORINE COATING AGENT HAVING ENHANCED DENTAL TUBULE PERMEABILITY AND COATING ENDURANCE AND METHOD FOR PREPARING SAME

(71) Applicant: OSSTEMIMPLANT CO., LTD., Seoul (KR)

(72) Inventors: Il Seok Jang, Yangsan-si (KR); Hanna Park, Busan (KR); Su Kyoung Kim, Busan (KR); Ju Dong Song, Busan (KR); Tae Gwan Eom, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 446 days.

(21) Appl. No.: 16/651,619

(22) PCT Filed: Sep. 28, 2018

(86) PCT No.: PCT/KR2018/011573
§ 371 (c)(1),
(2) Date: Mar. 27, 2020

(87) PCT Pub. No.: WO2019/066583
PCT Pub. Date: Apr. 4, 2019

(65) Prior Publication Data
US 2020/0297586 A1    Sep. 24, 2020

(30) Foreign Application Priority Data

Sep. 29, 2017   (KR) .................. 10-2017-0128012

(51) Int. Cl.
*A61K 6/887* (2020.01)
*A61K 6/20* (2020.01)

(52) U.S. Cl.
CPC ............... *A61K 6/887* (2020.01); *A61K 6/20* (2020.01)

(58) Field of Classification Search
None
See application file for complete search history.

(56) References Cited

U.S. PATENT DOCUMENTS

| 4,594,240 A | 6/1986 | Kawata et al. | |
| 11,407,986 B2* | 8/2022 | Regueira | C12N 9/2417 |
| 2011/0097368 A1* | 4/2011 | Jensen | A61K 8/21 |
| | | | 424/49 |

FOREIGN PATENT DOCUMENTS

| KR | 10-2001-0098785 A | 11/2001 | |
| KR | 20150122279 A | * 4/2015 | ............... A61K 6/20 |
| KR | 10-2015-0122279 A | 11/2015 | |
| KR | 2015-0122279 A | 11/2015 | |

OTHER PUBLICATIONS

Sule Bayrak et al, "Effect of fluoride varnish containing CPP-ACP on preventing enamel erosion.", Jan. 9, 2017, pp. 1-8.

* cited by examiner

*Primary Examiner* — Peter A Salamon
(74) *Attorney, Agent, or Firm* — Novick, Kim & Lee PLLC; Jae Youn Kim (57) ABSTRACT

A fluorine coating agent having enhanced dental tubule permeability and coating endurance, and a method for preparing the same. The fluorine coating agent applied on the surface of a tooth is enhanced in abrasion resistance to increase a period of time during which a coating membrane lasts, thereby preventing dental caries. Further, the curing time of the fluorine coating agent can be controlled to allow the agent to permeate and thus block the dental tubule.

5 Claims, 6 Drawing Sheets

| | NATURAL ROSIN | COMPARATIVE EXAMPLE 1 | EXAMPLE 1 |
|---|---|---|---|
| 1M (1260 BRUSHING MOTIONS) | | | |
| 3M (3780 BRUSHING MOTIONS) | | | |

FIG. 7

FLUORINE COATING AGENT HAVING ENHANCED DENTAL TUBULE PERMEABILITY AND COATING ENDURANCE AND METHOD FOR PREPARING SAME

TECHNICAL FIELD

The present invention relates to a fluoride coating agent with enhanced dentinal tubule penetrability and enhanced coating durability, which suppresses dentin hypersensitivity by enhancing dentinal tubule penetrability by adjusting a curing time of the fluoride coating agent to be applied on a tooth surface and imparts an anticariogenic effect to the tissue of teeth for a long period of time by enhancing coating durability by including high-molecular-weight poly(vinyl acetate) in the fluoride coating agent, and a preparation method thereof.

BACKGROUND ART

Dental caries develops when teeth are damaged due to chemical destruction caused by an acid, which is produced by the bacterial decomposition of nutrients (especially, monosaccharides) that the host ingests in dental plaque which is a mass of bacteria present in the oral cavity, dissolving a calcium salt among inorganic constituents of teeth.

Among various types of acids made by the bacteria of dental plaque, especially, lactic acid is so small in size that it can penetrate into the structure of the enamel of a tooth and thus cause severe damage to the internal enamel containing a relatively low amount of fluoride. This damage leads to the demineralization of calcium salts right under the tooth surface and the formation of larger and finer cavities under a tooth surface than those on the tooth surface, and the cavities are called white spots.

When the mechanism of development of dental caries is demineralization, the preventive mechanism thereof is remineralization. By inhibiting the development mechanism or restoring the initially formed caries to change the structure of the tooth surface through remineralization, it is possible to suppress the development or progression of the caries development mechanism.

A representative method used for the purpose of preventing dental caries is the use of fluoride-containing agents or materials. Since the application of the fluoride compound in an oral cavity promotes the remineralization of demineralized enamel, it can greatly help to treat tooth sensitivity to cold (dentin hypersensitivity) and prevent tooth decay (dental caries). In addition, since a coating film containing the fluoride compound is formed on teeth so as to strengthen enamel, it is possible to prevent tooth decay and promote a process of binding minerals such as calcium and the like to the teeth.

The mechanism of action of fluoride whereby dental caries is prevented or inhibited is effective, especially, for deciduous teeth containing a trace amount of fluoride. This is because the inclusion of fluoride in a crystal structure of enamel during the development of deciduous teeth results in the formation of a substance called fluoroapatite which is not dissolved well in an acid, and a large amount of fluoride is accumulated on a surface of enamel surrounded by body fluids, especially, immediately before deciduous teeth are developed in the oral cavity so as to rapidly increase the fluoride concentration, thereby apatite which is a crystal structure of the tooth surface has more chemical and physical stability.

According to the data of the oral health project of the Ministry of Health and Welfare, the representative oral care products using fluoride are divided into four categories: a fluoride dentifrice (fluoride-containing toothpaste-like product); a fluoride mouth rinse solution (fluoride-containing mouthwash-like product); a fluoride gel (product used by introducing the fluoride gel into a tray and keeping the tray in the mouth); and a fluoride coating agent (product applied together with pine resin which is natural rosin to keep fluoride adhered to the tooth surface for a long time).

Among these four categories, the fluoride coating agent is found to be most effective for preventing tooth decay, and the tooth decay prevention effect thereof is twice as high as that of the fluoride gel that was previously used. In addition, when the fluoride coating agent and the fluoride dentifrice are used together, it has been reported that the effect is improved by about 10%.

Since the conventional fluoride coating agent includes pine resin which is natural rosin tinged with red, the fluoride coating agent is not easily decomposed in a wet environment such as the oral cavity, easily adhered to the teeth due to having high adhesion to the teeth, and has high penetrability into dentinal tubules. However, the conventional fluoride coating agent imparts a high level of aesthetic rejection to patients due to the color change of the teeth after treatment with the fluoride coating agent and is maintained only for a short period of about 3 to 7 days after being applied on the teeth due to non-curing properties thereof, thereby the conventional fluoride coating agent could not be expected to have an effect of sustainedly preventing dental caries and suppressing dentin hypersensitivity.

In order to compensate for the disadvantages, photocurable fluoride coating agents having enhanced coating durability, high strength, and high hardness were developed. The photocurable fluoride coating agents can be expected to have the effect of preventing dental caries for a long period of time because a coating film is maintained for 1 month or more such that fluoride ions are sustainedly released but cannot be expected to have the effect of suppressing dentin hypersensitivity because a coating film is formed quickly as the photocurable fluoride coating agent is cured as soon as it is exposed to light such that the agent does not penetrate into dentinal tubules of the tooth and it is difficult to occlude dentinal tubules.

Therefore, the need for a fluoride coating agent, which is capable of sustainedly preventing dental caries by maintaining a coating film on the tooth surface for a long period of time and suppressing tooth sensitivity to cold caused by dentin hypersensitivity by occluding dentinal tubules while satisfying the aesthetic needs of patients and imparting procedure convenience and efficiency to operators, is increasing.

DISCLOSURE

Technical Problem

The present invention is directed to providing a fluoride coating agent with enhanced dentinal tubule penetrability and enhanced coating durability, which is capable of preventing dental caries by enhancing the abrasion resistance of the fluoride coating agent applied on a tooth surface to increase a period of time during which a coating film is maintained and also capable of occluding dentinal tubules by adjusting a curing time of the fluoride coating agent to penetrate the agent into dentinal tubules, and a preparation method thereof.

Technical Solution+

One aspect of the present invention provides a fluoride coating agent with enhanced dentinal tubule penetrability and enhanced coating durability, which includes high-molecular-weight poly(vinyl acetate) (PVAc) having a weight-average molecular weight of 300,000 to 600,000.

The fluoride coating agent may further include rosin, a fluoride compound, an emulsifier, and a solvent. In addition, the fluoride coating agent may further include low-molecular-weight poly(vinyl acetate) (PVAc) having a weight-average molecular weight of 1,000 to 150,000.

The fluoride coating agent may include the rosin at 15 to 35 wt %, the poly(vinyl acetate) at 8 to 25 wt %, the fluoride compound at 1 to 10 wt %, the emulsifier at 01 to 15 wt %, and a solvent at 27 to 71 wt %, wherein the poly(vinyl acetate) may be high-molecular-weight poly(vinyl acetate) or a mixture of high-molecular-weight poly(vinyl acetate) and low-molecular-weight poly(vinyl acetate).

The emulsifier may include at least one nonionic surfactant selected from the group consisting of glycol ethers, sorbitan fatty acid esters, alkyl polyglycosides, and alkoxylated alcohols.

The fluoride coating agent may have a viscosity of 800 to 1,500 cP.

Another aspect of the present invention provides a method of preparing a fluoride coating agent with enhanced dentinal tubule penetrability and enhanced coating durability, which includes: a first dissolution step in which high-molecular-weight poly(vinyl acetate) (PVAc) having a weight-average molecular weight of 300,000 to 600,000 is dissolved in a solvent to prepare a first solution; a second dissolution step in which rosin is dissolved in a solvent to prepare a second solution; and a mixing step in which the second solution, a fluoride compound, and an emulsifier are added to and stirred with the first solution.

In the first dissolution step, the first solution may be prepared by further including low-molecular-weight poly(vinyl acetate) (PVAc) having a weight-average molecular weight of 1,000 to 150,000.

The first dissolution step or the second dissolution step may be performed while heating to 45 to 75° C. in boiling water.

Advantageous Effects

Since a fluoride coating agent of the present invention includes high-molecular-weight poly(vinyl acetate), adhesion between a tooth surface and a fluoride coating agent is enhanced, and, simultaneously, the durability of a coating film formed by curing the agent is remarkably enhanced such that fluoride ions are sustainedly released in an oral cavity for a long period of time, thereby dental caries can be effectively prevented.

In addition, since the fluoride coating agent is allowed to sufficiently penetrate into dentinal tubules by adjusting a curing time of the fluoride coating agent so as to occlude dentinal tubules, dentin hypersensitivity is suppressed, and thus tooth sensitivity to cold can be relieved.

MODES OF THE INVENTION

Hereinafter, the present invention will be described in detail with reference to exemplary embodiments. Terms and words used in this specification and the claims should not be interpreted as limited to commonly used meanings or meanings in dictionaries and should be interpreted with meanings and concepts which are consistent with the technological scope of the invention.

Throughout the specification, a certain part "including" a certain element signifies that the certain part may further include, instead of excluding, another element unless particularly indicated otherwise.

Throughout the specification, "%" used to indicate the concentration of a specific substance means (weight/weight) % for solid/solid, (weight/volume) % for solid/liquid, and (volume/volume) % for liquid/liquid, unless otherwise indicated.

Hereinafter, a fluoride coating agent with enhanced dentinal tubule penetrability and enhanced coating durability and a preparation method thereof according to the present invention will be described in more detail.

First, the fluoride coating agent with enhanced dentinal tubule penetrability and enhanced coating durability according to the present invention may be applied onto a tooth surface and cured by volatilizing a solvent included in the fluoride coating agent so as to form a coating film. In this case, fluoride ions are sustainedly and slowly released from a fluoride compound included in the formed coating film, and, as a result, dental caries may be prevented.

Therefore, in order to prevent dental caries for a long period of time, the coating film, which is formed on the tooth surface by curing the fluoride coating agent, needs not to be peeled off by external stress such as food intake, masticatory movement, brushing, and the like and needs to have abrasion resistance and scratch resistance. In addition, by including a sufficient amount of a fluoride compound, the coating film needs to exhibit a sustained-release property with respect to fluoride ions so that fluoride ions are sustainedly released.

For this purpose, the fluoride coating agent with enhanced dentinal tubule penetrability and enhanced coating durability according to the present invention includes high-molecular-weight poly(vinyl acetate) (PVAc) having a weight-average molecular weight of 300,000 to 600,000 so as to enhance adhesion between the coating film formed by curing the fluoride coating agent and the tooth surface and exhibit resistance to abrasion caused by external stress, and, as a result, the coating film may be maintained on the tooth surface for a long period of time.

Meanwhile, the fluoride coating agent with enhanced dentinal tubule penetrability and enhanced coating durability according to the present invention may further include rosin, a fluoride compound, an emulsifier, and a solvent in addition to the high-molecular-weight poly(vinyl acetate).

The rosin is a base material of the fluoride coating agent and is not easily decomposed in a wet environment such as the oral cavity. Therefore, the rosin exhibits high chemical safety, an adhesion impartment effect, and high compatibility with various types of elastic resins.

In addition, the rosin is not particularly limited as long as it is typically used as medical and food materials, has adhesion to the teeth, and is able to be dissolved in a solvent, and gum rosin- or wood rosin-based compounds may be used as the rosin.

As one example, the rosin may be one or more selected from the group consisting of natural rosin, dehydrogenated rosin, esters of hydrogenated rosin, fully hydrogenated rosin, partially hydrogenated rosin, dimerized rosin, and hydrocarbon resin.

The rosin may be included at 15 to 35 wt % in the total composition of the fluoride coating agent of the present invention. When the content of the rosin included in the fluoride coating agent is less than 15 wt %, it may not be expected to have sufficient adhesion to the teeth. On the other hand, when the content of the rosin is more than 35 wt %, not only spreadability is degraded due to an increase in viscosity when the coating agent is applied onto the teeth such that procedure convenience may be lowered but also a thick coating layer is formed on the tooth surface such that a subject to be treated may feel discomfort.

Meanwhile, by sustainedly releasing fluoride ions, the fluoride compound included in the fluoride coating agent serves to strengthen enamel, prevent tooth decay, and promote a process of binding minerals such as calcium and the like to the teeth.

The fluoride compound included in the fluoride coating agent is not particularly limited as long as it is not toxic to the human body and is capable of releasing fluoride ions. For example, one or more selected from the group consisting of sodium fluoride (NaF), sodium monofluorophosphate ($Na_2PFO_3$), stannous fluoride ($SnF_2$), bismuth trifluoride ($BiF_3$), zinc fluoride ($ZnF_2$), potassium fluoride (KF), calcium fluoride ($CaF_2$), zirconium tetrafluoride ($ZrF_4$), hexafluorosilicic acid ($H_2SiF_6$), and sodium hexafluorosilicate ($Na_2SiF_6$) may be used as the fluoride compound.

As one example, the fluoride ions released from the fluoride compound included in the fluoride coating agent bond with hydrogen ions present in the oral cavity to form hydrogen fluoride (HF), and the formed hydrogen fluoride penetrates into the inside of bacteria. The hydrogen fluoride penetrating into the bacteria may acidify the inside of the bacterial cells while being dissolved, and fluoride may inhibit the glycolysis of the cells. When fluoride accumulates in the bacterial cells, harmful bacteria in the oral cavity are killed, and accordingly, the fluoride ions in the oral cavity may prevent tooth decay.

In addition, the fluoride ions released from the fluoride compound promote the remineralization of demineralized enamel. Also, the fluoride ions take the hydroxyl ion sites of hydroxyapatite which is the main component of the tooth so as to form fluoroapatite which is harder than hydroxyapatite on the tooth surface. Accordingly, demineralization is prevented by inhibiting the loss of minerals from enamel, and thus dental caries may be prevented.

The fluoride compound may be included at 1 to 10 wt % in the total composition of the fluoride coating agent of the present invention. When the content of the fluoride compound is less than 1 wt %, it may be difficult to expect a desired effect of preventing tooth decay, and when the content of the fluoride compound is more than 10 wt %, adhesion between the tooth and the fluoride coating agent may be degraded due to an excessive amount of the fluoride compound.

The fluoride compound may have an average particle diameter of 0005 to 100 μm. When the average particle diameter of the fluoride compound is less than 0005 μm, it may be difficult to uniformly disperse fluoride compound particles in the fluoride coating agent due to cohesion between particles. On the other hand, when the average particle diameter of the fluoride compound is more than 100 μm, the applicability of the fluoride coating agent is degraded such that it may be difficult to apply the fluoride coating agent onto the teeth of a subject to be treated, and, even after application, fluoride compound particles are likely to be lost by saliva or the tongue, thereby the release of fluoride ions may be reduced.

Meanwhile, after the fluoride coating agent with enhanced dentinal tubule penetrability and enhanced coating durability according to the present invention is applied onto the tooth surface, the solvent included in the fluoride coating agent may be volatilized to form a coating film on the tooth surface.

However, when the fluoride coating agent is quickly cured on the tooth surface, the fluoride coating agent starts to be cured before penetrating into dentinal tubules, and thus dentinal tubules are not completely occluded, and when the fluoride coating agent is slowly cured, the duration of a procedure may be prolonged until the fluoride coating agent is completely cured. Therefore, a curing time needs to be adjusted by the preferred viscosity of the fluoride coating agent.

A viscosity or curing time of the fluoride coating agent of the present invention may be adjusted using the solvent or the emulsifier.

The emulsifier may adjust a viscosity of the fluoride coating agent and, simultaneously, impart chemical stability to prevent phase separation in which the solvent and a solute such as the rosin, fluoride compound, poly(vinyl acetate), and the like are separated.

The emulsifier may include at least one nonionic surfactant selected from the group consisting of glycol ethers, sorbitan fatty acid esters, alkyl polyglycosides, and alkoxylated alcohols, and glycol ethers and sorbitan fatty acid esters are preferably used.

In addition, the emulsifier may be included at 01 to 15 wt % in the fluoride coating agent of the present invention. When the content of the emulsifier is outside the above-described preferred range, phase separation of the fluoride coating agent occurs, or a curing time of the fluoride coating agent is prolonged, thereby procedure convenience may be lowered.

As described above, when the fluoride coating agent with enhanced dentinal tubule penetrability and enhanced coating durability according to the present invention is applied onto the teeth, the fluoride coating agent is cured by volatilizing the solvent included in the fluoride coating agent so as to form a coating film.

Therefore, as the solvent included in the fluoride coating agent, a volatile solvent may be used. For example, one or more selected from the group consisting of ethanol, isopropyl alcohol, acetone, benzene, cyclohexane, toluene, n-pentane, n-hexane, n-heptane, n-octane, ethyl acetate, methyl acetate, and isopropyl acetate may be used as the solvent.

The content of the solvent included in the fluoride coating agent of the present invention may affect the spreadability of the fluoride coating agent, the degree of formation of a coating film, and dispersibility. The solvent may be included at 27 to 71 wt % in the fluoride coating agent and may be used by appropriately adjusting the content thereof with the preferred range according to the storage method, the period of use, the mode of use, and the method of use of the fluoride coating agent.

Since the fluoride coating agent with enhanced dentinal tubule penetrability and enhanced coating durability according to the present invention includes high-molecular-weight poly(vinyl acetate) having a weight-average molecular weight of 300,000 to 600,000, the stretch resistance of a coating film formed by applying the fluoride coating agent on the tooth surface is enhanced, and thus the coating film may be maintained for a long period of time. While the coating film is maintained for a long period of time, fluoride ions are sustainedly released in the oral cavity, and thus dental caries (tooth decay) may be prevented.

The fluoride coating agent may further include low-molecular-weight poly(vinyl acetate) (PVAc) having a weight-average molecular weight of 1,000 to 150,000 in addition to the high-molecular-weight poly(vinyl acetate) so as to enhance the adhesion of the fluoride coating agent to the teeth.

The fluoride coating agent may include the poly(vinyl acetate) at 8 to 25 wt % with respect to the total weight of the fluoride coating agent, and the poly(vinyl acetate) may be high-molecular-weight poly(vinyl acetate) or a mixture of high-molecular-weight poly(vinyl acetate) and low-molecular-weight poly(vinyl acetate).

When the content of the poly(vinyl acetate) is less than 8 wt % of the fluoride coating agent, a coating film formed on the tooth surface is easily peeled off or worn by external stress, and thus it may be difficult to expect a dental caries prevention effect. On the other hand, when the content of the poly(vinyl acetate) is more than 27 wt %, it is difficult to form a thin coating film due to an increase in viscosity of the fluoride coating agent such that a subject to be treated may feel discomfort, and applicability is degraded such that procedure convenience may be lowered.

In addition, since the fluoride coating agent with enhanced dentinal tubule penetrability and enhanced coating durability according to the present invention has an appropriate curing rate, the fluoride coating agent penetrates into and occludes dentinal tubules of the tooth, and thus dentin hypersensitivity may be suppressed to relieve "tooth sensitivity to cold". Therefore, the fluoride coating agent needs to have a viscosity of 800 to 1,500 cP. When the viscosity of the fluoride coating agent is outside the above-described preferred range, the applicability of the fluoride coating agent may be degraded to lower procedure convenience, the fluoride coating agent may not sufficiently penetrate into dentinal tubules due to a low or high curing rate, or the duration of a procedure may be prolonged.

The fluoride coating agent with enhanced dentinal tubule penetrability and enhanced coating durability according to the present invention may further include known active ingredients that may be typically added to enhance oral health such as whitening teeth, strengthening enamel, and the like, and these active ingredients may be further included in a pharmaceutically and functionally effective amount within a range which does not adversely affect the effect of the present invention.

For example, the active ingredients may include nonionic disinfectants such as isopropyl methylphenol and the like, cationic disinfectants such as cetylpyridinium chloride, benzalkonium chloride, benzethonium chloride, and the like, anti-inflammatory agents such as tranexamic acid, ε-aminocaproic acid, allantoin, glycyrrhetinic acid, glycyrrhizic acid, and the like, enzymes such as dextranase, mutanase, amylase, proteases, lysoteam, and the like, fluorides such as sodium fluoride and the like, water-soluble phosphate compounds such as potassium salts of orthophosphoric acid and the like, copper compounds such as copper gluconate, sodium copper chlorophyllin, and the like, inorganic salts such as sodium chloride, silicon dioxide, potassium nitrate, zinc chloride, zinc citrate, strontium chloride, and the like, vitamins such as ascorbic acid, tocopherol acetate, and the like, plant extracts such as chlorophyll extracts, *Angelica gigas* root soft extracts, *Thymus vulgaris* extracts, *Scutellaria baicalensis* root extracts, clove extracts, *Hamamelis virginiana* extracts, and the like, desensitizers including an anti-calculus agent, an anti-plaque agent, and casein phosphopeptide-amorphous calcium phosphate (CPP-ACP) which suppresses dentin hypersensitivity, and the like.

Meanwhile, another aspect of the present invention provides a method of preparing a fluoride coating agent with enhanced dentinal tubule penetrability and enhanced coating durability, which include: a first dissolution step in which high-molecular-weight poly(vinyl acetate) (PVAc) having a weight-average molecular weight of 300,000 to 600,000 is dissolved in a solvent to prepare a first solution; a second dissolution step in which rosin is dissolved in a solvent to prepare a second solution; and a mixing step in which the second solution, a fluoride compound, and an emulsifier are added to and stirred with the first solution.

The solvent, rosin, fluoride compound, and emulsifier used in the method of preparing a fluoride coating agent have been described above, so detailed descriptions thereof will be omitted.

In the first dissolution step, high-molecular-weight poly(vinyl acetate) (PVAc) having a weight-average molecular weight of 300,000 to 600,000 is dissolved in the solvent to prepare the first solution, and a diluted solvent may be used to dissolve the high-molecular-weight poly(vinyl acetate) which is an organic compound having a high molecular weight.

As the solvent used in the first dissolution step, preferably, a solvent obtained by diluting, in water, one or more selected from the group consisting of ethanol, isopropyl alcohol, acetone, benzene, cyclohexane, toluene, n-pentane, n-hexane, n-heptane, n-octane, ethyl acetate, methyl acetate, and isopropyl acetate which are volatile solvents, more preferably a solution diluted to a concentration of 91 to 97%, and most preferably 92 to 96% ethanol may be used. This is because the high-molecular-weight poly(vinyl acetate) is not sufficiently dissolved when a 100% volatile solvent is used instead of a diluted solution.

In addition, when the high-molecular-weight poly(vinyl acetate) is dissolved using the diluted solvent, low-molecular-weight poly(vinyl acetate) may be further included.

As one example, a first solution may be prepared by heating a 92 to 96% volatile solvent to 45 to 75° C. in boiling water and then adding high-molecular-weight poly(vinyl acetate) or a mixture of high-molecular-weight poly(vinyl acetate) and low-molecular-weight poly(vinyl acetate) to the solvent.

In the second dissolution step, rosin is dissolved in the volatile solvent to prepare the second solution. The volatile solvent used herein may be the same solvent as used in the first dissolution step or a 100% volatile solvent. This is because the rosin has higher solubility in the volatile solvent than the high-molecular-weight poly(vinyl acetate) such that it is possible to dissolve the rosin at a sufficiently high concentration using a 100% volatile solvent rather than a diluted solution obtained by diluting the volatile solvent in the second dissolution step.

As one example, a second solution may be prepared by heating a 100% volatile solvent to 45 to 75° C. in boiling water, then adding rosin thereto, and dissolving the rosin in the solvent.

Subsequently, a fluoride compound and an emulsifier are added to and mixed with the first solution and the second solution prepared in the first dissolution step and the second dissolution step to prepare a fluoride coating agent with enhanced dentinal tubule penetrability and enhanced coating durability.

In the mixing step, the above-described known active ingredients that may be typically added to enhance oral health such as whitening teeth, strengthening enamel, and the like may be further included.

Hereinafter, examples of the present invention will be described. However, the scope of the present invention is not limited to the following exemplary examples, and various modifications of the contents described herein may be made by those skilled in the art without departing from the scope of the present invention.

PREPARATION EXAMPLE

Preparation of Fluoride Coating Agent

First, poly(vinyl acetate) (PVAc) having weight-average molecular weights as shown in Table 1 below was dissolved in 94% ethanol while heating to 65° C. in boiling water to prepare a 30% PVAc solution (first solution).

Then, rosin was dissolved in 94% ethanol while heating to 65° C. in boiling water to prepare a 70% rosin solution (second solution).

Figure 1:
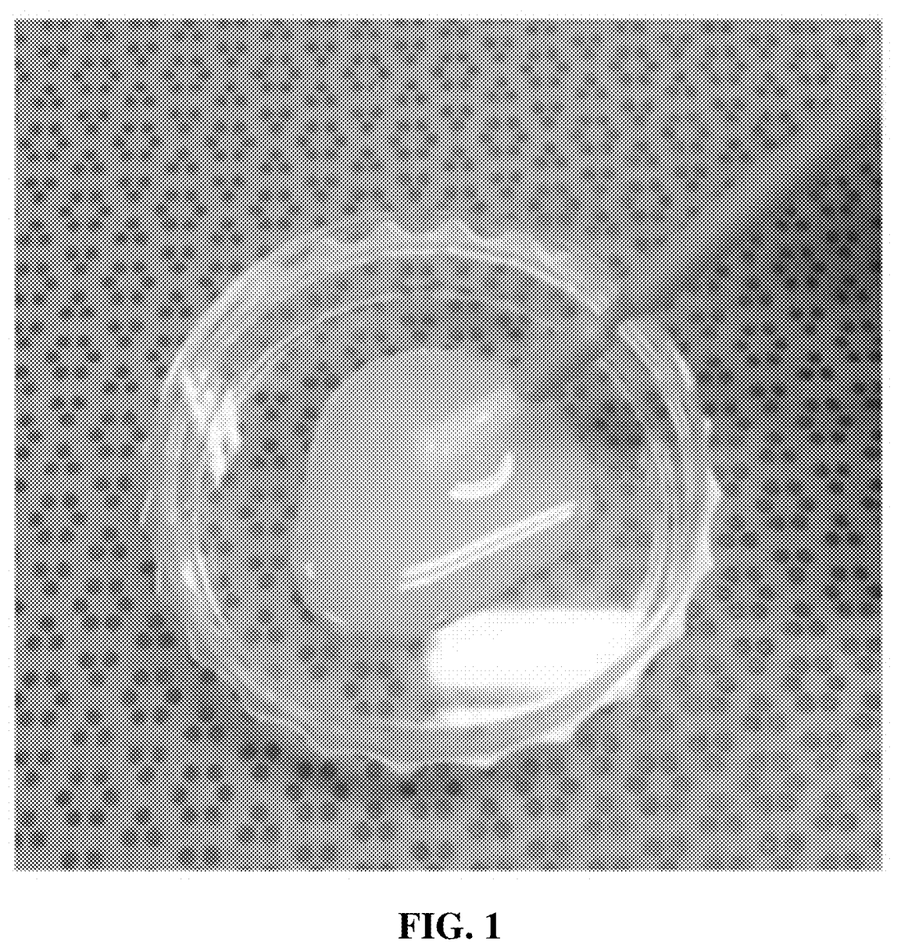
FIG. 1 is a photographic image of a fluoride coating agent with enhanced dentinal tubule penetrability and enhanced coating durability, which is prepared according to the example of the present invention.

The first solution was mixed with the second solution, a fluoride compound, casein phosphopeptide-amorphous calcium phosphate (CPP-ACP), silicon dioxide, potassium nitrate, and an emulsifier in contents as shown in Table 1 below to prepare a fluoride coating agent of Example 1 as shown in FIG. 1 and a fluoride coating agent of Comparative Example 2.

TABLE 1

| Classification | | Example 1 | Comparative Example 1 |
|---|---|---|---|
| Poly(vinyl acetate) | High molecular weight (500,000) | 10 | — |
| | Low molecular weight (80,000) | — | 20 |

TABLE 1-continued

| Classification | | Example 1 | Comparative Example 1 |
|---|---|---|---|
| | Hydrogenated rosin | 30 | 30 |
| | Fluoride compound (NaF) | 5 | 5 |
| Active ingredients | CPP-ACP | 1.5 | 1.5 |
| | Silicon dioxide | 1 | 1 |
| | Potassium nitrate | 0.5 | 0.5 |
| Emulsifiers | Sorbitan fatty acid ester (Tween 80) | 1.5 | — |
| | Glycol ether (Cellosove) | — | 10 |
| | Solvent | 50.5 | 32 |
| | Total | 100 | 100 |

(Units: wt %)

Experimental Example 1

Phase Separation Phenomenon According to Emulsifier Condition

1) Observation of Phase Separation Phenomenon According to Presence or Absence of Emulsifier First, in order to confirm a phase separation phenomenon according to the presence or absence of an emulsifier, a control (B) was prepared in the same manner as in Example 1 (A) of the preparation example except that a solvent was further included instead of an emulsifier.

10 ml each of Example 1 (A) and the control (B) was introduced into respective conical tubes and maintained at room temperature for 45 days, and then whether phase separation occurred was observed.

Figure 2:
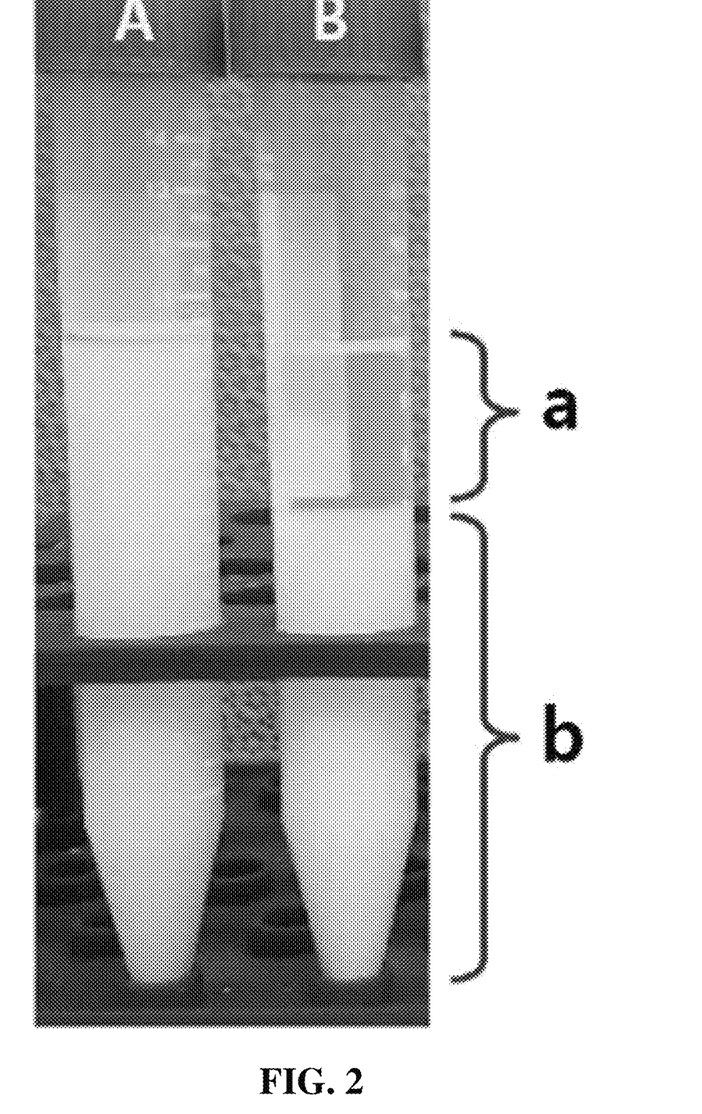
FIG. 2 is a photographic image showing experimental results of observing a phase separation phenomenon according to the presence or absence of an emulsifier in accordance with an experimental example of the present invention.

As shown in FIG. 2, after 45 days, in the case of Example 1 (A) including an emulsifier, it can be seen that almost no phase separation was observed. On the other hand, in the case of the control (B) including no emulsifier, it can be seen that a supernatant (a) and a precipitate (b), in which poly(vinyl acetate) which is a polymer, hydrogenated rosin, active ingredients, and a fluoride compound were precipitated, were separated, indicating that phase separation occurred.

2) Observation of phase separation phenomenon according to type of emulsifier and molecular weight of poly(vinyl acetate)

A control was prepared in the same manner as in Example 1 of the preparation example except that a solvent was further included instead of an emulsifier, and Comparative Example 2 was prepared in the same manner as in Comparative Example 1 except that high-molecular-weight poly(vinyl acetate) was used instead of low-molecular-weight poly(vinyl acetate).

10 ml each of the control, Comparative Example 1, Comparative Example 2, and Example 1 was introduced into respective conical tubes and maintained at room temperature. After 1 month and 2 months had elapsed, phase separation (%) was determined using the following Formula (1), and results thereof are shown in FIG. 3.

$$\text{Phase separation (relative \%)} = (\text{Volume (ml) of precipitate})/(10\ ml) \times 100 \quad \text{Formula (1)}$$

Figure 3:
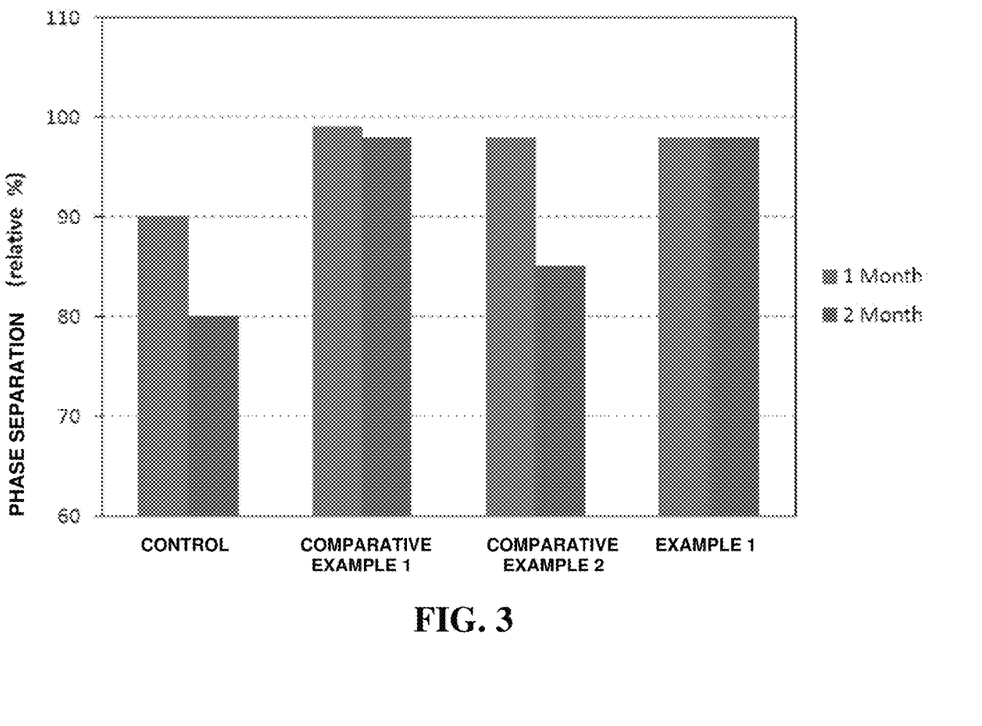
FIG. 3 is a graph showing experimental results of observing a phase separation phenomenon according to the type of emulsifier and a molecular weight of poly(vinyl acetate) in accordance with an experimental example of the present invention.

Referring to the results shown in FIG. 2 and FIG. 3, in the case of the control including no emulsifier, it can be seen that a phase separation phenomenon was observed after 1 month.

Meanwhile, as a result of comparing Comparative Example 1 prepared using a glycol ether as an emulsifier and low-molecular-weight poly(vinyl acetate) and Comparative Example 2 prepared using a glycol ether as an emulsifier and high-molecular-weight poly(vinyl acetate), it can be seen that Comparative Example 1 prepared using low-molecular-weight poly(vinyl acetate) did not exhibit significant phase separation even after 2 months, whereas Comparative Example 2 prepared using high-molecular-weight poly(vinyl acetate) exhibited significant phase separation after 2 months. However, in the case of Example 1 prepared using a sorbitan fatty acid ester as an emulsifier, it can be seen that there was almost no phase separation even after 2 months.

From this result, it can be seen that, since low-molecular-weight poly(vinyl acetate) having a weight-average molecular weight of less than 150,000 has relatively high solubility in a solvent compared to high-molecular-weight poly(vinyl acetate), when Comparative Examples 1 and 2 includes the same amount and component of an emulsifier (glycol ether), Comparative Example 2 including high-molecular-weight poly(vinyl acetate) exhibits phase separation over time.

However, in the case of Example 1 including a sorbitan fatty acid ester having superior emulsifying capacity to a glycol ether, it can be seen that, even when high-molecular-weight poly(vinyl acetate) was included, phase separation did not occur after 2 months.

From this result, it can be seen that it is preferable that the fluoride coating agent of the present invention, which includes high-molecular-weight poly(vinyl acetate), includes a sorbitan fatty acid ester as an emulsifier.

Experimental Example 2

Thickness of Coating Film According to Viscosity of Fluoride Coating Agent

While adjusting the viscosity of the fluoride coating agent by further adding a solvent to Example 1, the thickness of a coating film was confirmed according to the viscosity.

In this case, the viscosity of the fluoride coating agent was measured by collecting 1 cc of individual agents using a viscometer (microVISC viscometer, RheoSense Inc., USA)

The coating thickness was measured using a scanning electron microscope (SEM) image. A discomfort experiment was performed by forming coating films using the fluoride coating agent on the teeth of 10 subjects to be treated and then observing whether the subjects feel discomfort (feeling discomfort: O/feeling no discomfort: X).

TABLE 2

| Viscosity (cP) | ~200 | 800~1,500 | 3,000~5,000 |
|---|---|---|---|
| Coating thickness (um) | <2 | 5~10 | 30< |
| Discomfort | X | X | O |
| Abrasion resistance | Highly likely to be removed by external stress due to thin coating layer | Less likely to be removed by external stress due to coating layer having appropriate thickness | Highly unlikely to be removed by external stress due to thick coating layer |

Figure 4:
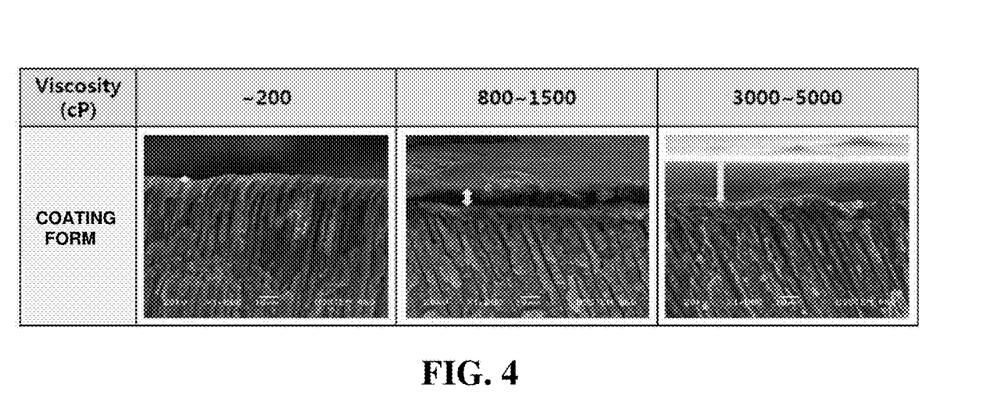
FIG. 4 is a scanning electron microscope (SEM) image showing results of observing a thickness of a coating film formed of a fluoride coating agent of the present invention according to a viscosity of the fluoride coating agent.

Referring to the results shown in Table 2 and FIG. 4, in the case of having low viscosity (200 cP or less), the coating film formed on the tooth surface is so thin that the coating film is highly likely to be removed by external stress such as brushing or food intake. On the other hand, in the case of having high viscosity (3,000 to 5,000), the coating film formed on the tooth surface is so thick that the subjects to be treated feel discomfort. Therefore, it is preferable that the fluoride coating agent has a viscosity of 800 to 1,500 cP.

Experimental Example 3

Measurement of Penetrability of Fluoride Coating Agent into Dentinal Tubules

1) Comparison of Penetrability of Fluoride Coating Agents into Dentinal Tubules (SEM Analysis)

Figure 5:
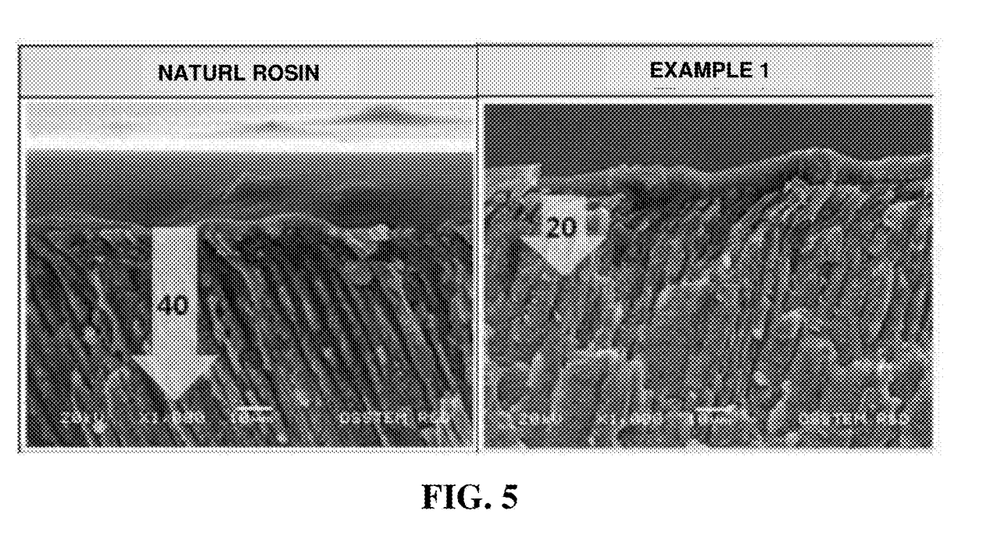
FIG. 5 is an SEM image showing results of observing the dentinal tubule penetrabilities of a fluoride coating agent of the present invention and a fluoride coating agent prepared using natural rosin.

The dentinal tubule penetrabilities of a fluoride coating agent prepared using natural rosin and the fluoride coating agent of Example 1 were observed through an electron microscope, and results thereof are shown in FIG. 5.

From the result shown in FIG. 5, it can be seen that the fluoride coating agent prepared using natural rosin penetrated deep into dentinal tubules, whereas the fluoride coating agent of Example 1 of the present invention penetrated into dentinal tubules so as to occlude the dentinal tubules, thereby it was expected to suppress dentin hypersensitivity and prevent tooth sensitivity to cold.

2) Measurement of dentinal tubule permeability (dentin permeability-digital measurement) according to molecular weight of poly(vinyl acetate) and emulsifier included in fluoride coating agent In order to confirm whether the fluoride coating agent occludes dentinal tubules by penetrating into dentinal tubules and whether the fluoride coating agent still occludes dentinal tubules even after external stress (brushing) was applied thereto, dentinal tubule permeability was measured.

Figure 6:
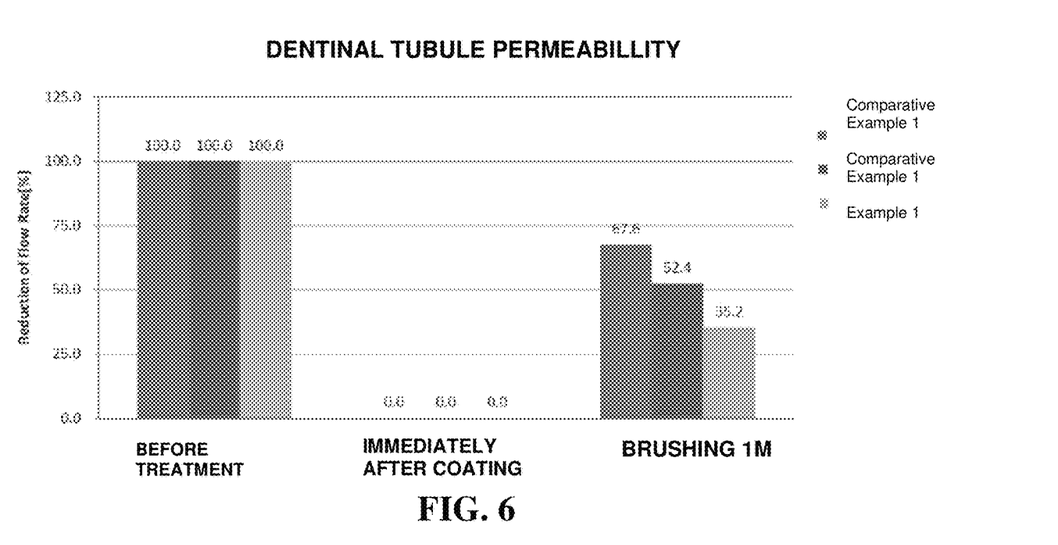
FIG. 6 is an SEM image showing results of observing dentinal tubule penetrability according to the type of emulsifier and a molecular weight of poly(vinyl acetate) in accordance with an experimental example of the present invention.

To measure dentinal tubule permeability, the permeability of dentin was measured using a dentin permeability test of Odeme Dental Research, and a change in dentinal tubule permeability was measured according to conditions such as: before the fluoride coating agent was applied (before treatment); immediately after the fluoride coating agent was applied and completely cured (immediately after treatment); and after external stress was applied to the sample by brushing the sample with a toothbrush weighing 320 to 450 g (3 times a day for 1 month, 15 brushing motions at a time, 1 M (4 weeks); total of 1,260 brushing motions), and results thereof are shown in FIG. 6.

From the result shown in FIG. 6, it can be seen that, since nothing penetrated into dentinal tubules of the teeth before the fluoride coating agents were applied, all of Comparative Examples 1 and 2 and Example 1 were confirmed to be 100% permeability, whereas, immediately after the fluoride coating agents were applied, all of Comparative Examples 1 and 2 and Example 1 were confirmed to be 0% permeability.

However, as a result of measuring dentinal tubule permeability after the samples were brushed 3 times a day for 1 month, in the case of Comparative Examples 1 and 2, it can be seen that the coating films were damaged by external stress, and thus dentinal tubule permeability was increased.

On the other hand, it can be seen that, since Example 1 of the present invention which included high-molecular-weight poly(vinyl acetate) had high coating durability, dentinal tubule permeability was lower than Comparative Examples 1 and 2. From this result, it can be seen that Example 1 of the present invention may prevent dental caries by maintaining the coating film for a long period of time and relieve tooth sensitivity to cold by occluding dentinal tubules.

Experimental Example 4

Measurement of Coating Durability of Fluoride Coating Agent

In order to measure the coating durability of the fluoride coating agent applied onto the teeth, each of a fluoride coating agent prepared using natural rosin, the fluoride coating agent of Comparative Example 1, and the fluoride coating agent of Example 1 was applied and completely cured on a sample made of the same composition as human teeth.

The samples in which coating films had been formed by curing the fluoride coating agents were repeatedly brushed, and then the abrasion degree of the coating films was confirmed through an electron microscope.

Weight of toothbrush applied to sample: 320 to 450 g

Brushing Number: 3 times a day, 15 one-way brushing motions at a time

1 M (4 weeks); 1,260 brushing motions/3 M (12 weeks); 3,780 brushing motions

Figure 7:
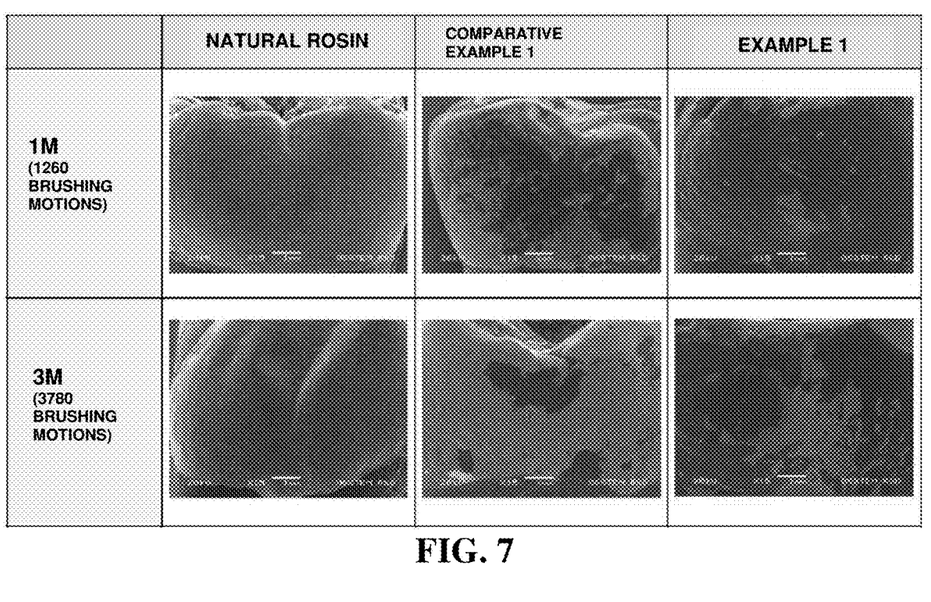
FIG. 7 is an SEM image showing results of observing the durabilities of a coating film formed of a fluoride coating agent of the present invention and a coating film formed of a fluoride coating agent prepared using natural rosin.

Referring to the result shown in FIG. 7, in the case of the fluoride coating agent prepared using natural rosin, it can be seen that the coating film was completely removed after 1 month of the brushing. In the case of Comparative Example 1, it can be seen that, even when about half of the coating film remained after 1 month of the brushing, the coating film was almost removed after 3 months of the brushing.

On the other hand, in the case of Example 1 of the present invention, it can be seen that the coating film still remained even after 3 months of the brushing.

The invention claimed is:

1. A fluoride coating agent with enhanced dentinal tubule penetrability and enhanced coating durability, the fluoride coating agent comprising high-molecular-weight poly(vinyl acetate) (PVAc) having a weight-average molecular weight of 300,000 to 600,000 at 8 to 25 wt %, rosin at 15 to 35 wt %, a fluoride compound at 1 to 10 wt %, an emulsifier at 0.1 to 15 wt %, and a solvent at 27 to 71 wt %,
    wherein the emulsifier includes sorbitan fatter acid esters, and
    the fluoride coating agent has a viscosity of 800 to 1,500 cP.

2. The fluoride coating agent of claim 1, further comprising low-molecular-weight poly(vinyl acetate) (PVAc) having a weight-average molecular weight of 1,000 to 150,000.

3. A method of preparing a fluoride coating agent with enhanced dentinal tubule penetrability and enhanced coating durability of claim 1, the method comprising:
    a first dissolution step in which high-molecular-weight poly(vinyl acetate) (PVAc) having a weight-average molecular weight of 300,000 to 600,000 is dissolved in a solvent to prepare a first solution;
    a second dissolution step in which rosin is dissolved in a solvent to prepare a second solution; and
    a mixing step in which the second solution, a fluoride compound, and an emulsifier are added to and stirred with the first solution.

4. The method of claim 3, wherein, in the first dissolution step, the first solution is prepared by further including low-molecular-weight poly(vinyl acetate) (PVAc) having a weight-average molecular weight of 1,000 to 150,000.

5. The method of claim 3, wherein the first dissolution step or the second dissolution step is performed while heating to 45 to 75° C. in boiling water.

* * * * *